(12) United States Patent
Ilan

(10) Patent No.: US 10,786,681 B2
(45) Date of Patent: Sep. 29, 2020

(54) CLOSED LOOP ORGAN STIMULATION

(71) Applicant: Yaron Ilan, Kefar Tavor (IL)

(72) Inventor: Yaron Ilan, Kefar Tavor (IL)

( * ) Notice: Subject to any disclaimer, the term of this patent is extended or adjusted under 35 U.S.C. 154(b) by 248 days.

(21) Appl. No.: 15/889,463

(22) Filed: Feb. 6, 2018

(65) Prior Publication Data
US 2018/0221678 A1 Aug. 9, 2018

Related U.S. Application Data

(60) Provisional application No. 62/455,666, filed on Feb. 7, 2017.

(51) Int. Cl.
*A61N 2/00* (2006.01)
*A61N 2/02* (2006.01)
*A61F 7/00* (2006.01)
*A61F 7/12* (2006.01)
*A61F 7/02* (2006.01)

(52) U.S. Cl.
CPC .............. *A61N 2/006* (2013.01); *A61N 2/02* (2013.01); *A61F 7/00* (2013.01); *A61F 7/12* (2013.01); *A61F 2007/0022* (2013.01); *A61F 2007/0228* (2013.01)

(58) Field of Classification Search
CPC ................................ A61N 2/006; A61N 2/02
USPC ........................................................ 600/9–15
See application file for complete search history.

(56) References Cited

FOREIGN PATENT DOCUMENTS

| KR | 20150003606 | 1/2015 |
|----|-------------|--------|
| WO | 2015087324  | 6/2015 |
| WO | 2016033118  | 3/2016 |
| WO | 2017002104  | 1/2017 |

OTHER PUBLICATIONS

Horbach, et al, abiliti Closed-loop gastric electrical stimulation system for treatment of obesity: clinical results with a 27-month follow-up, Obesity Surgery, 2015, pp. 1779-1787, vol. 25, No. 10.

*Primary Examiner* — John P Lacyk
(74) *Attorney, Agent, or Firm* — The Roy Gross Law Firm, LLC; Roy Gross

(57) ABSTRACT

The present disclosure provides systems, devices and methods for providing abdominal or any other organ stimulation for affecting a physiological change, wherein the stimulation parameters are continuously, semi continuously, or conditionally being updated based on measurements and inputs provided to a computer circuitry configured to facilitate machine learning capabilities.

17 Claims, 5 Drawing Sheets

CLOSED LOOP ORGAN STIMULATION

TECHNICAL FIELD

The present disclosure generally relates to the field of abdominal or any organ stimulation for affecting a physiological change.

BACKGROUND

Commonly, treatments or interventions intended to affect a physiological change, are carried out based on predetermined protocols, such that once a certain treatment protocol is prescribed/configured, it stays the same until the treatment is finished.

This is especially the case in stimulation interventions, such as abdominal or brain stimulation interventions, where a stimulation protocol is set at one point, and is not changed afterwards.

While these methods show effectiveness in some cases, they are less effective or sometimes not effective at all in other cases. This is mainly because not all subjects react the same physiologically to the same stimulation protocol and also due to adaptation of the activated organ which prevents long term effect of the stimulation.

There is thus a need in the art for more effective methods of organ stimulation that take into consideration the variability between subjects and their physiological reaction to stimulation as well as to enable long-term effect of the stimuli.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other advantages or improvements.

According to some embodiment, there are provided herein devices, systems and methods for abdominal or any other organ stimulation, wherein the stimulation parameters are updated within the treatment/stimulation period, for personalizing the stimulation parameters and increasing the accuracy and efficacy of the stimulation treatment for achieving the desired physiological goal as well as to prevent long-term adaptation for ensuring prolonged effect of the stimuli on the target organ or physiological pathway.

According to some embodiments, the parameters are determined and updated using a machine learning system, which provides parameter values based on feature values received from and/or related to the user.

According to some embodiments, the machine learning system is a deep learning system, in which the learning on some features is guided learning, while learning on other features is unguided learning.

According to some embodiments, the number of layers/levels of the deep machine learning depends on the number of features or on the number of associations between them.

According to some embodiments, the user updates the machine with inputs indicative of progress towards the target physiological effect goal, and the learning machine provides updated stimulation parameters based on data learned from the user and/or other users, while a different weight may be given to other users with similar feature values such as race, age, gender, health conditions and so on, as well as data specific to the user, for example progress towards target weight and the like.

According to some embodiments, as used herein, the term physiological goal or target may refer to value. Once the goal is achieved, the stimulation may change only to maintain it, or, for example, when the user gets closer to the target value, the stimulation changes, such as "slows down".

According to some embodiments, as used herein, the term physiological goal or target may refer to a gradient or change in a physiological measure/parameter in a desired direction. For example, the goal may be losing weight and not necessarily achieving a specific weight. In this case, such a goal may be a weight loss or the like, without setting or determining an exact value as a target for the physiological measure/parameter.

According to some embodiments, a user may update the machine, or the machine may receive inputs from the user and/or from other users which are being used to update the algorithm in a way that enables it to redirect or further define the stimuli being administered to the user following a closed-loop system. According to some embodiments, newly generated stimuli further contribute to progression towards a target physiological effect goal, and the learning machine provides updated stimulation parameters based on data being continuously learned from other users. According to some embodiments, the data received is continuously or semi-continuously analyzed based on subgroups of patients, including based on disease parameters, targets of physiological levels to be achieved, as well as age, gender, concomitant diseases and others.

According to some embodiments, there is provided a system for closed loop abdominal (or brain or any other organ) stimulation, comprising: an update module, computationally configured to receive a plurality of feature values, and provide stimulation parameters based thereon; a sensor, configured to measure a physiological property and provide a signal indicative thereof; a stimulation device, comprising: a stimulation inducer, configured to generate a stimulation action based on stimulation parameters to affect a physiological change in a target (organ or organs); and a communication unit, configured to allow transfer of data to the stimulation device for modifying one or more stimulation parameters, and an update module, comprising a processing circuitry, configured to: obtain a signal from the sensor; determine stimulation parameters based on the signal obtained from the sensor; provide the stimulation device with the determined stimulation parameters via the communication unit.

According to some embodiments, the processing circuitry of the update module is operated to facilitate machine learning capabilities, wherein supervised and/or unsupervised learning is utilized.

According to some embodiments, the stimulation is provided for achieving a desired physiological change, and the learning machine success factor is achieving and maintaining this physiological change.

According to some embodiments, the physiological goal is a lowering bodyweight, managing glucose levels, and/or lowering blood pressure. According to some embodiments, the machine learning capabilities include deep learning capabilities. According to some embodiments, the features of the machine learning are selected from a list comprising: age, weight, periodic caloric intake and output, gender, ethnicity, geography, pathological history/state, temperature, metabolic rate, glucose levels, blood tests and any physiological or pathological parameters that can be measured, whether directly or indirectly associated with the physiological target.

According to some embodiments, the stimulation inducer is configured to affect a stimulation by providing a magnetic signal to a target body part, by physical movement, by electromagnetic signal emission, by temperature alteration, by including pressure, or using various types of rate and rhythms of stimuli with various frequencies, amplitudes, durations, and interval, in structured or random manner (or other types of direct or indirect stimuli).

According to some embodiments, the sensor is configured to measure temperature, oxygen levels, blood pressure, and/or blood tests (and/or any physiological or pathological parameters that can be measured whether directly or indirectly associated with the physiological target).

According to some embodiments, there is provided a stimulation device for abdominal stimulation, comprising: a stimulation inducer, configured to generate a stimulation action based on stimulation parameters to affect a physiological change in a target region (which may be any organ); and a communication unit, configured to allow transfer of data between the stimulation device and an update module; wherein the update module comprises a processing circuitry, configured to: obtain a signal from a sensor indicative of a physiological property; determine stimulation parameters based on the signal obtain from the sensor; provide the stimulation device with the determined stimulation parameters via the communication unit.

According to some embodiments, the device may have a form of a pill, configured to be swallowed or transplantable and reach a target body region within the digestive track (or any other organ in the body).

According to some embodiments, the device may have a form of a wearable device, configured to be placed/held on/near a target body region (or in other places).

According to some embodiments, the stimulation inducer is configured to affect a stimulation by providing a magnetic signal to a target body part, by physical movement, by electromagnetic signal emission, by temperature alteration, by including pressure, and/or any combination thereof (in various types of rates and/or rhythms of stimuli, any/or type of direct or indirect stimuli).

According to some embodiments, the sensor is configured to measure temperature, oxygen levels, pressure and/or, body weight.

According to some embodiments, there is provided a method for a (continuous, semi-continuous, conditional, or non-continuous) closed loop abdominal stimulation, comprising: providing/placing in a proximity of a target body part a stimulation device with a stimulation inducer; providing initial stimulation parameters to the device based on initial acquired information and a desired physiological change; providing stimulation via the stimulation inducer based on the initial stimulation parameters; obtain information from the user and/or device or other sources, and update the stimulation parameters based on the obtained information.

According to some embodiments, updating the stimulation parameters includes utilizing machine learning capabilities. According to some embodiments, the machine learning capabilities include deep learning. The machine learning capabilities may be configured to be operated on a set of features by receiving values thereof.

According to some embodiments, the stimulation device is an implantable device. According to some embodiments, the stimulation device is configured to be swallowed by a user. According to some embodiments, the stimulation device is configured to be placed on the body of the user.

According to some embodiments, the physiological goal is a reduction of weight and/or maintaining a weight loss. According to some embodiments, the method is applied for treatment of obesity, and/or any metabolic, inflammatory, infectious and/or malignant condition.

The embodiments disclosed herein may apply for inducing and/or maintaining weight loss, the treatment of obesity or any metabolic, inflammatory, infectious, or malignant condition with an ability to stimulate the brain, heart, muscles, nerves, kidney, lungs, bowel, or any other organ or sub organ in the body, using devices/systems/methods/algorithms disclosed herein.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION

Figure 1:
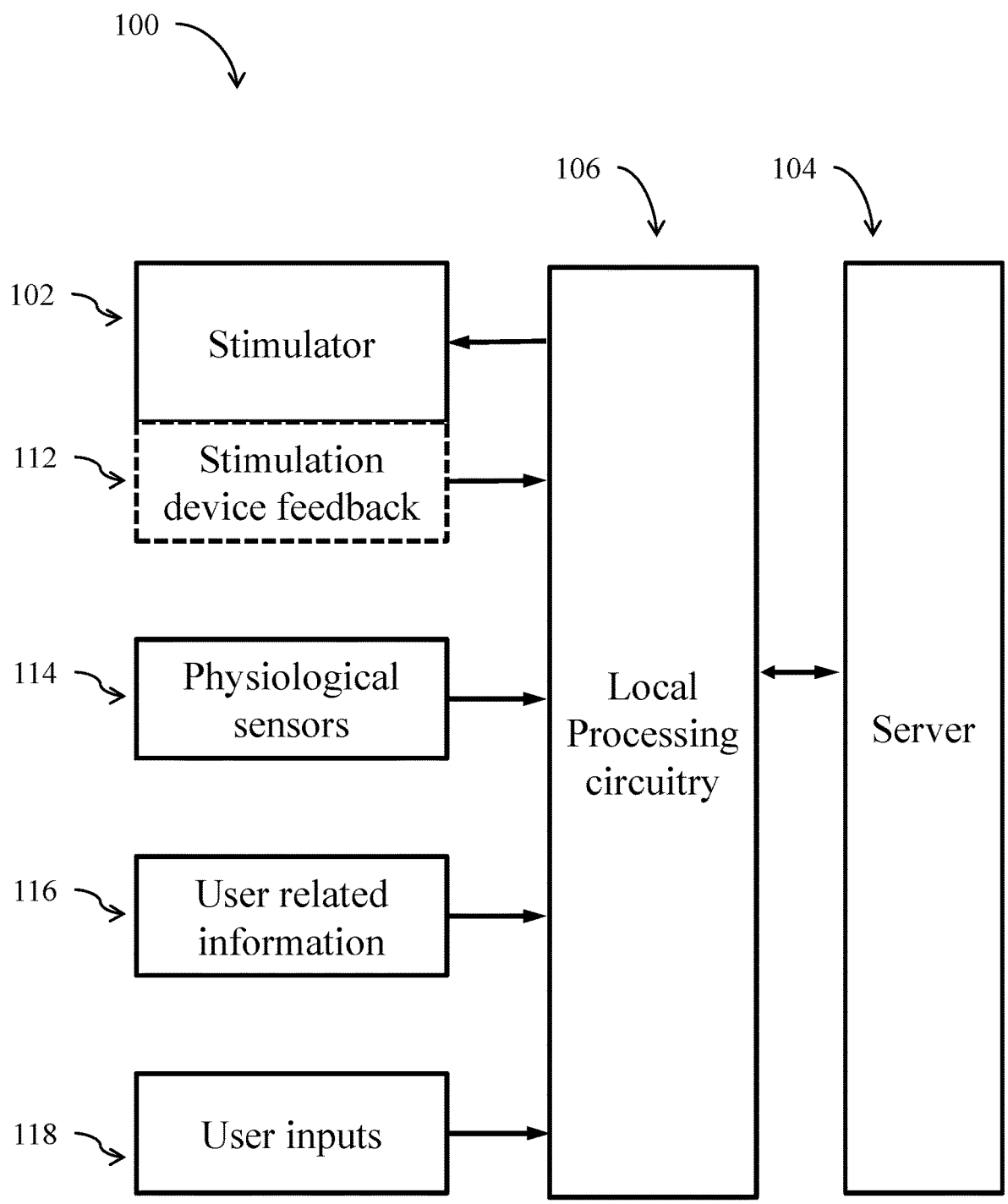
FIG. 1 schematically illustrates a functional block diagram of an abdominal stimulation system, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

According to some embodiments, there are provided herein devices, systems and methods for abdominal or any other organ stimulation, wherein the stimulation parameters are updated within the treatment/stimulation period, for personalizing the stimulation characteristics to increase the accuracy and efficacy of the stimulation treatment for achieving the desired physiological goal.

According to some embodiments, the parameters are determined and updated using a machine learning system, which provides parameter values based on feature values received from and/or related to the user.

According to some embodiments, the machine learning system is a deep learning system, in which the learning on some features is guided learning, while learning on other features is unguided learning.

According to some embodiments, the number of layers/levels of the deep machine learning depends on the number of features.

According to some embodiments, the user updates the machine with progress towards the target physiological effect goal, and the learning machine provides updated stimulation parameters based on data learned from the user and/or other users, with a different weight that may be given to other users with similar feature values such as race, age, gender, health conditions and so on, as well as data specific to the user, for example progress towards target weight and the like.

According to some embodiments, user inputs may include caloric intake, physical activity and others. According to some embodiments, inputs indicative of physical activity may be derived from measurements of the location or movements of the user, for example by utilizing GPS or accelerator sensors.

According to some embodiments, the user may update the machine or the machine may receive inputs (for example, from the user, from other users and/or from other sources, such as weight meter, smartphone app to measure activity, fitness watch or other wearables etc.) which are being used to update the algorithm in a way that enables it to redirect or further define the stimuli being administered to the user following a closed-loop system. According to some embodiments, the newly generated stimuli may further contribute to progression towards a target physiological effect goal. The learning machine provides updated stimulation parameters based on data being continuously learned from the user and/or other users. The data received is being continuously analyzed based on subgroups of patients including based on disease parameters, targets of physiological levels to be achieved, as well as age, gender, concomitant diseases, caloric intake, physical activity, and others.

As used herein, the terms "learning machine", "update module" and "update system" are interchangeably used, and refer to an integrated or communicatively linked component of the system, which is configured to receive input data in form of user data (such as weight, medical state, gender age and the like) in addition to features (such as measurements of directly or indirectly relevant bodily indications) and generates based thereon a stimulation parameter, a set of stimulation parameters or a series of stimulation parameters forming stimulation plan(s) based on the current inputs, historic inputs and/or preconfigured data from the user, multiple users and/or models of users.

According to some embodiments, the input data on the user, along with the input received from other users on a continuous basis, is being processed by the controller, which, based on a closed loop system that continuously evaluates the distance of the tested parameter from the level to be achieved or the direction and/or rate of changes in the physiological measurement/parameter, generates an improved algorithm being transformed into new stimuli.

Reference is now made to FIG. 1, which schematically illustrates a functional block diagram of an abdominal stimulation system 100, according to some embodiments. According to some embodiments, system 100 includes a stimulator 102 or stimulation inducer, which is configured to provide stimulation to a target body part (generally abdominal, brain, or any other organ in the body), to achieve a desired physiological effect, optionally one feedback mechanism 112 associated with stimulator 102, configured to provide measurements of physiological indictors such as temperature, pressure, impedance, and the like from the target body part or a proximity thereof, or alternatively, technical information related to stimulator 102, such as battery charge level. These parameters may be related or non-directly related to the physiological target which the algorithm is aimed at improving.

According to some embodiments, system 100 may further include additional external sensors 114, for example, for measuring blood oxidation or coming from results of blood tests or any other test and the like, which, along with the information from feedback mechanism 112 are provided to a local processing circuitry 106 which is configured to control the operation of stimulator 102 based on inputs that include measurements of external or internal sensors 114, and optional feedback mechanism 112. According to some embodiments, processing circuitry 106 is further configured to obtain inputs of user related information 116 and other user inputs 118, based on which the stimulation parameters are determined.

According to some embodiments, external sensor 114 may be a weight sensor, configured to provide local processing circuitry 106 with information indicative of the weight of the user at certain times. According to some embodiments, a user may be instructed or advised to measure their weight periodically, at certain times or after/at/before certain events.

According to some embodiments, processing circuitry 106 may be in communication with a remote server 104 for tapping into the computing performance thereof, and/or data of previous/other users. According to some embodiments, remote server 104 may be a cloud computer.

According to some embodiments, processing circuitry 106 is designed for a continuous closed loop data input and output, wherein stimulation parameters are adjusted based on the input information and data.

According to some embodiments, the stimulation device may be introduced to provide stimulation from within the human body, for example as a capsule swallowed by the user, or placed at certain positions to affect the desired stimulation.

According to some embodiments, the stimulation device may be introduced to provide stimulation from within the human body, for example as a transplantable device to be placed at certain positions to affect the desired stimulation or an ingestible object (like a capsule).

Figure 2:
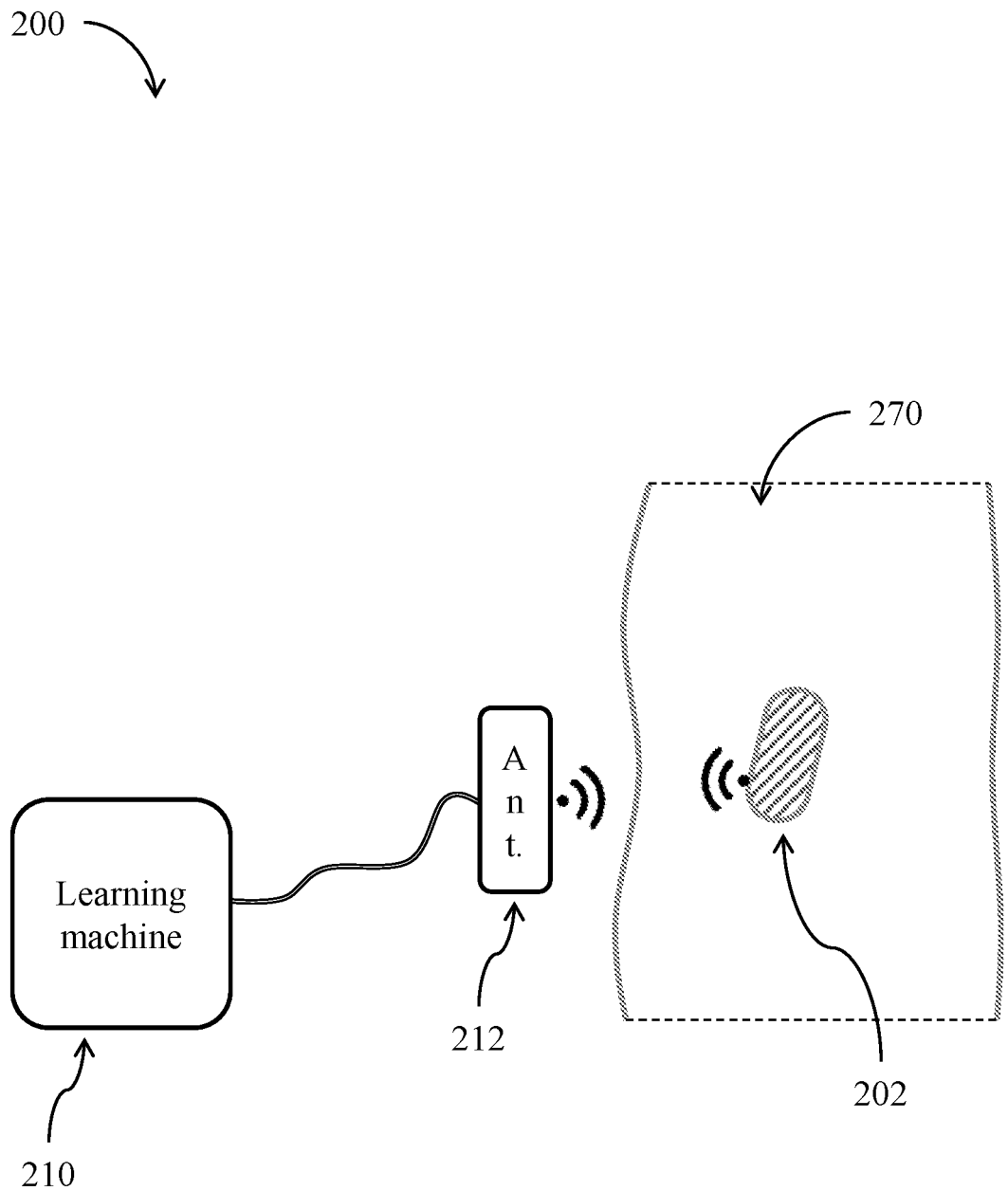
FIG. 2 schematically illustrates an internal abdominal or any other organ stimulation system, according to some embodiments.

Reference is now made to FIG. 2, which schematically illustrates an internal abdominal or any other organ stimulation system 200, according to some embodiments. According to some embodiments, system 200 includes a stimulation device 202, configured to be inserted to be introduced to a target area of a subject 270, to induce stimulation thereto.

According to some embodiments, stimulation device 202 is in communication with an update module, such as learning machine 210 via a wireless communication link, such as through antenna 212, for sending sensor information (in case, there is a sensor in stimulation device 202) from stimulation device 202 to learning machine 210, and receiving updated stimulation parameters therefrom, to adjust the stimulation and achieve desired results towards reaching the target goal of a physiological feature. It is noted that stimulation device 202 may or may not include a sensor.

According to some embodiments, stimulation techniques may include magnetic, electric, electromagnetic, mechanical, thermal or the like. According to some embodiments, changes in stimulation characteristics may include variations or changes in stimulation patterns(repetitions), frequency, intensity, and duration. According to some embodiments, stimulation may be provided continuously or intermittently with On/Off time periods, and the duration of the time periods and/or the ration between them may be changed in either a structured manner, randomly or semi-randomly.

Figure 3:
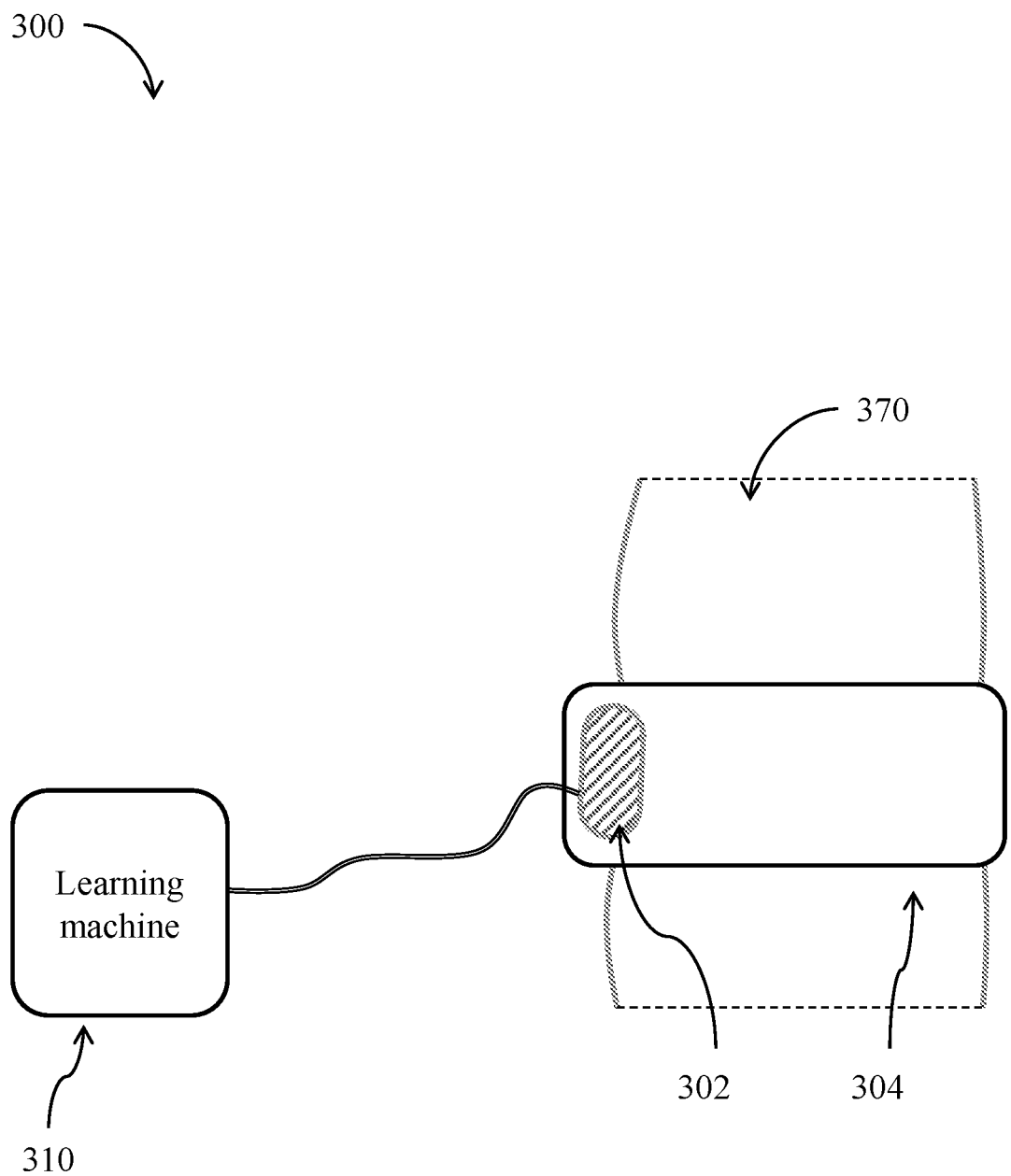
FIG. 3 schematically illustrates an external abdominal or other organ stimulation system, according to some embodiments.

Reference is now made to FIG. 3, which schematically illustrates an external abdominal or any other organ stimulation system 300, according to some embodiments. According to some embodiments, system 300 includes a stimulation device 302, which is configured to be placed at a desired position on the body of the participant 370 to induce stimulation thereto, for example by being fastened using a strap/belt 304.

According to some embodiments, stimulation device 302 is in communication with an update module, such as learning machine 310, for updating stimulation parameters/characteristics. According to some embodiments, the communication may be wireless.

According to some embodiments, both external and internal devices can be used both for data collection and input of data from various organs and/or for the generation of the stimuli required for achieving a target physiological goal. The closed loop system is continuously or semi continuously receiving data from internal and external measured parameters from one or many users, and are continuously being processed by the controller for generating a new stimuli to be administered to the user via an internal or external device.

According to some embodiments, the update-unit/learning-machine is updated upon changes in the measured information, or, for example, if the change is greater than a certain percentage of the previous value, or if the values reach a predetermined threshold, or any combination of the above.

Figure 4:
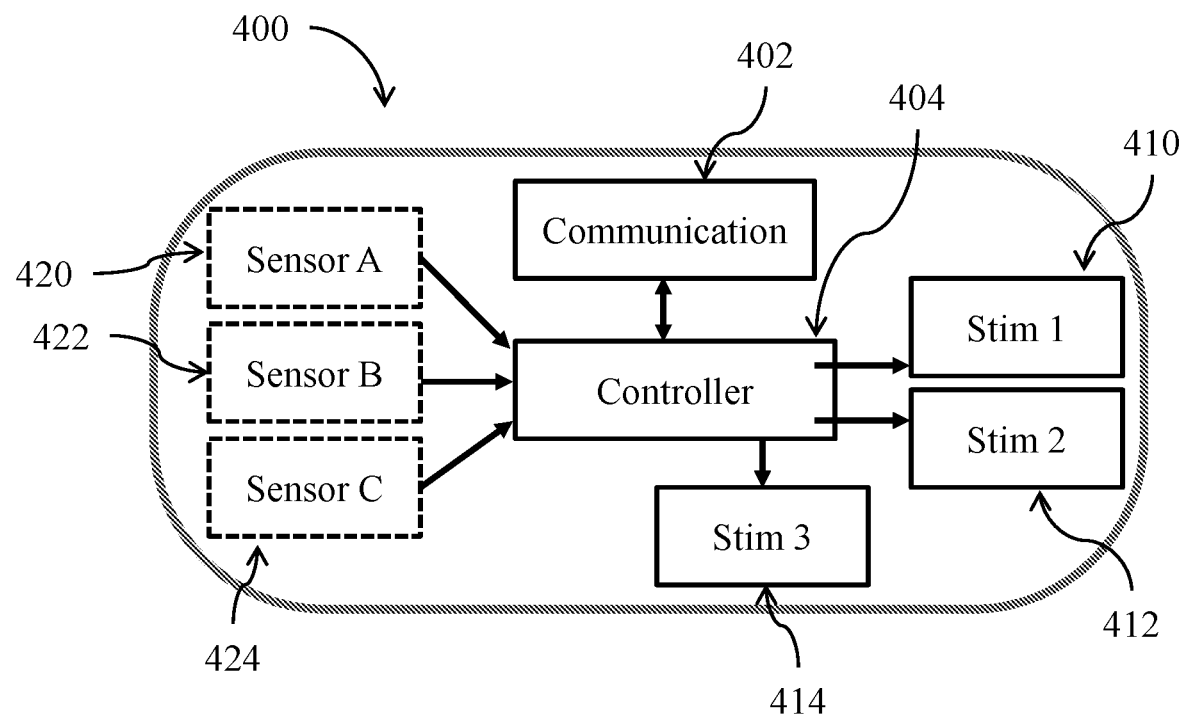
FIG. 4 schematically illustrates a functional block diagram of an internal or external stimulation device, according to some embodiments, and FIG. 5 schematically illustrates a method for providing updated parameters for abdominal or other organ stimulation, according to some embodiments.

Reference is now made to FIG. 4, which schematically illustrates a functional block diagram of an internal stimulation device 400, according to some embodiments. According to some embodiments, stimulation device 400 is in a form of a pill or any other internal device 400, and includes a first stimulation inducer 410, a second stimulation inducer 412, and a third stimulation inducer 414, configured to provide stimulation using different stimulation techniques, or different directionalities.

According to some embodiments, stimulation device 400 may optionally further includes sensors, such as optional sensor A 420, optional sensor B 422, and optional sensor C 424, in addition to a controller 404, configured to control the operation of first stimulation inducer 410, second stimulation inducer 412, and third stimulation inducer 414 to achieve a physiological change towards a physiological goal, according to stimulation parameters that are received via a communication unit 402, which is configured to be in communication with an external or internal update module/unit/circuitry for receiving the stimulation parameters, and sending thereto information from the sensors, or other operational information.

According to some embodiments, the stimulation device may include non transitory memory for storing stimulation sessions to be provided to the user. According to some embodiments, the stimulation device does not include memory thereon for storing stimulation session, but is rather controlled by the update-unit for changing the stimulation parameters whenever such a change takes place.

Figure 5:
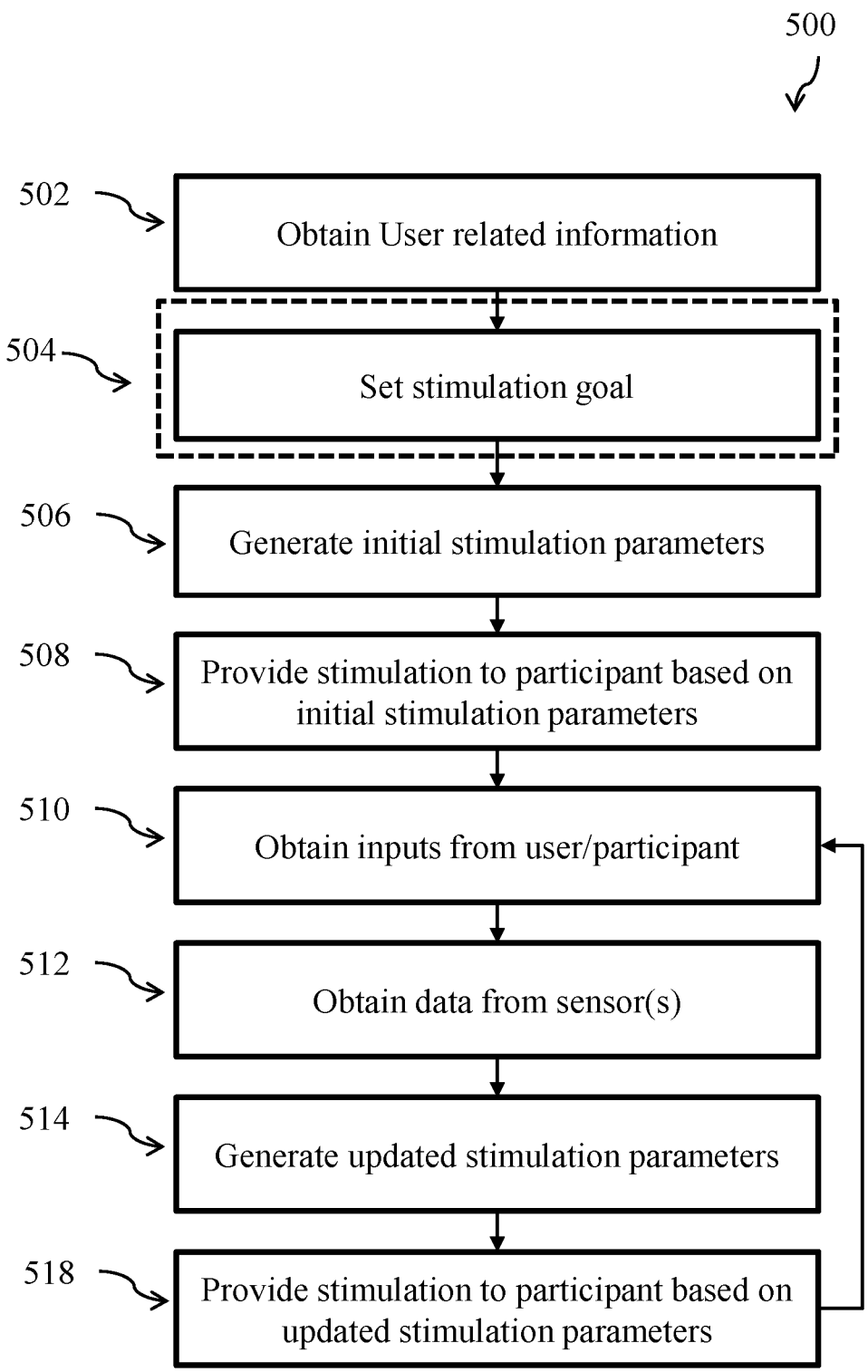

Reference is now made to FIG. 5, which schematically illustrates a method 500 for providing updated parameter abdominal or any other stimulation, according to some embodiments. According to some embodiments, method 500 begins by obtaining user related information (step 502) which may be sensor measurements, or more general information such as weight, dimensions, gender, clinical history and the like; then, if there is no general goal, a stimulation physiological goal is set (step 504) which may include a target body weight, glucose levels, blood pressure levels, improvement of function of any organ which is not well functioning, or any organ which is affected by inflammatory, infectious, or malignant process, or a change to a positive direction of one or more of the abovementioned physiological parameters, such as reduction in weight and/or reduction in blood pressure. Accordingly, initial stimulation parameters are determined (step 506) and provided to a participant (step 508). Then, input is provided to the device, which may include updated weight or other measures (step 510), or sensor data (step 512), and then updated stimulation parameters are generated accordingly (step 514) and stimulation is provided to the participant based on the updated parameters (step 518), and then back to step 510 for closed loop stimulation.

According to some embodiments, the system can continuously receive input from internal and external devices from multiple patients which is being processed according to a deep machine learning algorithm such that relevant data from other users is being applied to the specific patient to optimize the type of stimuli being generated for him. In that way, a patient-tailored algorithm is generated based on input from the patient and relevant data from other users or patients.

According to some embodiments, the deep machine learning algorithm is designed to have several levels of closed loops which are built one on top of the other but also function in parallel to enable the generation of an optimized stimuli enabling reaching the physiological target.

According to some embodiments, the update system (update module) may have a dual local and network architecture, in which, for example, the local unit/circuitry is in real-time or short-delay loop with the stimulation device, and updates the stimulation parameters without involving a higher level computational circuitry, such as a server or a cloud computer. And the update system may also include a global/network component thereto, wherein inputs may be received from multiple users, and learning from the data of the multiple users may be applied in the stimulation parameters of individual users.

Advantageously, in such a local-global architecture, the stimuli may be updated in a short/immediate closed-loop using the lower level (local) update module, wherein a longer and less immediate closed-loop may update the stimuli using the higher level (global) update module.

The two-stage hierarchical architecture of the update system brought above is exemplary, and other conceptually similar architectures may apply in various embodiments.

As used herein, the term "update system" or "update module" refers to a component configured to be in wired or wireless communication with the stimulation device for set and amend stimulation parameters.

According to some embodiments, each data parameter which is received and analyzed with correlation to the stimuli generated and thus the algorithm can determine the type of data, or features, which is most relevant for the specific user/patient which correlate with the physiological target or desired physiological change. This input parameter may not be identical to all users/patients and may not be identical for the same user/patient regarding different physiological targets, objectives or improvements.

According to some embodiments, the stimulation characteristics may change over time even for the same user with the same desired physiological change, and even if there is a positive physiological change. Such changes in stimulation characteristics may be done for avoiding habituation of the user to the stimulation, and maintaining a positive physiological change.

Disclosed herein is an example of the use of a closed loop continuously learning algorithm for prevention of weight regain.

The target population is patients with BMI of 25-35.

The physiological target: of reaching a weight with a BMI of less than 24.

The stimulation device (internal or external device) receives data from the sensors (internal and external), indicative of body weight, pulse, and breathing, skin conductivity along with hunger and satiety hormones at fasting condition.

The input data is processed in correlation with the physiological target to assess whether an improvement was achieved, and to what extent. And if no improvement towards the target was achieved, a new stimuli is being generated. If a positive step towards the target weight was achieved, the controller will then divide each type of stimuli into 100 percentiles that determines the percentile for each of the components of the stimuli (such as rate of stimuli, rhythm, power, frequency, amplitude and temperature, or others, or any combination thereof) and which order of administration or alternating between them which was the most efficient in contributing to the achievement of the physiological change, such as weight loss. Based on that analysis, a new stimuli is generated. In general, the machine learning computer implemented method may require a plurality of weight samples for learning the user and providing effective stimulations.

The stimulation parameters update mechanism/algorithm is configured to continuously narrow the range or change the order by which the stimuli are being administered, to be targeted on the most effective stimulation characteristics for the specific user.

The stimulation characteristics/parameters update mechanism/algorithm is configured to learn from indications/ measurements (measured parameters) which may not be directly related to weight. These include, for example, blood tests of electrolytes, blood oxygen.

According to some embodiments, the algorithm operated in the update module may take into consideration outliers from the plurality of users, to which the learnings of the general users may not fit, and develop new models of treatment (new decision structures) for such outliers.

The algorithm, per one patient, may be developed based on big data analysis generated from multiple patients. It is noted that the stimuli generated by the big data can be further analyzed by age, gender, body weight, delta of weight decrease over time, concomitant diseases, geographic location, weather conditions, concomitant medications, and other parameters; it may not be identical per all patients, and is only a contributing level of data to the deep machine learning algorithm which generated a patient-tailored algorithm.

According to some embodiments, the algorithm may change over time per each patient, such that a decrease from BMI of 30 to 29 may not require the same stimuli as that of decreasing from 29 to 28. As the algorithm is continuously learning, it will change itself continuously based on both the data being accumulated by the big data and from each patient.

For example, a stimuli that is being generated by a belt on the abdomen that can generates two types of stimuli (vibration and heat) with three stimulation parameters:

Frequency, intermittency (intervals between On and Off periods), and power/temperature.

The table below shows the number of parameters that can be generated by a belt:

|  | No of stimuli |
|---|---|
| Assuming 1 per second | 1 |
| Per minute | 60 |
| Per 12 minutes | 720 |
| Per day | 1440 |
| Per 3 engines | 4320 |
| Per 3 parameters | 12960 |
| Calculated order of administration | 167961600 |
| Divided per deciles | 16796160 |
| Total per patient per day | 16796160 |
| Total per patient per week | 117573120 |
| Total per patient per month | 503884800 |
| Total per 1000 patients per month | 5.03885E+11 |

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising," when used in this specification, specify the presence of stated features, integers, steps, operations, elements, or components, but do not preclude or rule out the presence or addition of one or more other features, integers, steps, operations, elements, components, or groups thereof.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

The invention claimed is:

1. A system for closed loop abdominal stimulation, comprising:
   an update module, computationally configured to receive a plurality of feature values, and provide stimulation parameters based thereon;
   a sensor, configured to measure a physiological property, and provide a signal indicative thereof;
   a stimulation device, comprising:
      a stimulation inducer, configured to generate a stimulation action based on stimulation parameters to affect a physiological change in a target organ or organs; and a communication unit, configured to allow transfer of data to the stimulation device for modifying one or more stimulation parameters, and wherein the update module comprises, a processing circuitry, configured to:
obtain a signal from said sensor;
determine stimulation parameters based on the signal obtained from said sensor; and
provide said stimulation device with the determined stimulation parameters via said communication unit,
wherein said processing circuitry of the update module is utilizing a deep learning system, in which the learning on some features is guided learning, while learning on other features is unguided learning.

2. The system of claim 1, wherein the stimulation is provided for achieving a desired physiological change.

3. The system of claim 2, wherein the desired physiological change is a lowering of bodyweight, managing glucose levels, and/or lowering blood pressure.

4. The system of claim 1, wherein the feature values are selected from a list comprising: age, weight, periodic caloric intake and output, gender, ethnicity, geography, pathological history/state, temperature, metabolic rate, glucose levels, blood tests and any physiological or pathological parameters that can be measured whether directly or indirectly associated with the physiological target.

5. The system of claim 1, wherein said stimulation inducer is configured to affect a stimulation by providing a magnetic signal to a target body part, by physical movement, by electromagnetic signal emission, by temperature alteration, by including pressure, or using various types of rate and rhythms of stimuli with various frequencies, amplitudes, durations, and interval, in structured or random manner.

6. The system of claim 1, wherein the sensor is configured to measure, temperature, oxygen levels, blood pressure, and/or blood tests.

7. A stimulation device for abdominal stimulation, comprising:
a stimulation inducer, configured to generate a stimulation action based on stimulation parameters to affect a physiological change in a target region; and
a communication unit, configured to allow transfer of data between the stimulation device and an update module;
wherein the update module comprises a processing circuitry, configured to:
obtain a signal from a sensor indicative of a physiological property;
determine stimulation parameters based on the signal obtain from said sensor; and
provide said stimulation device with the determined stimulation parameters via said communication unit,
wherein said processing circuitry of the update module is utilizing a deep learning system, in which the learning on some features is guided learning, while learning on other features is unguided learning.

8. The device of claim 7, having a form of a pill, configured to be swallowed or transplantable and reach a target body region within the digestive track.

9. The device of claim 7, having a form of a wearable device, configured to be placed/held on/near a target body region.

10. The device of claim 7, wherein said stimulation inducer is configured to affect a stimulation by providing a magnetic signal to a target body part, by physical movement, by electromagnetic signal emission, by temperature alteration, and/or by including pressure, or by any combination thereof.

11. The device of claim 7, wherein the sensor is configured to measure, temperature, oxygen levels, pressure and/or body weight.

12. A method for a continuous, semi-continuous, conditional, or non-continuous closed loop abdominal stimulation, comprising:
providing/placing in a proximity of a target body part the stimulation device of claim 9;
providing initial stimulation parameters to the stimulation device based on initial acquired information and a desired physiological change;
providing stimulation via the stimulation inducer based on the initial stimulation parameters; and
obtain information from the user and/or device or other sources, and update the stimulation parameters based on the obtained information.

13. The method of claim 12, wherein the stimulation device is an implantable device.

14. The method of claim 12, wherein the stimulation device is configured to be swallowed by a user.

15. The method of claim 12, wherein the stimulation device is configured to be placed on the body of the user.

16. The method of claim 12, wherein the physiological change is a reduction of weight and/or maintaining a weight loss.

17. The method of claim 16, for treatment of obesity, and/or any metabolic, inflammatory, infectious and/or malignant condition.

* * * * *